United States Patent
Williams, III et al.

(10) Patent No.: US 7,282,165 B2
(45) Date of Patent: Oct. 16, 2007

(54) WEAR RESISTANT HYDROGEL FOR BEARING APPLICATIONS

(75) Inventors: Philip F. Williams, III, Teaneck, NJ (US); Chau Ngo, Secaucus, NJ (US); Christopher DeMaria, Glen Rock, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 526 days.

(21) Appl. No.: 10/832,852

(22) Filed: Apr. 27, 2004

(65) Prior Publication Data

US 2005/0236742 A1    Oct. 27, 2005

(51) Int. Cl.
*B05B 3/00* (2006.01)

(52) U.S. Cl. .................. 264/28; 264/425; 264/488; 264/478

(58) Field of Classification Search .............. 264/28, 264/494, 29.6, 349, 226, 219, 222; 524/916; 525/326.3; 252/182.13; 427/213.33; 623/13.12; 604/368; 514/772.2
See application file for complete search history.

(56) References Cited

U.S. PATENT DOCUMENTS

| | | | |
|---|---|---|---|
| 3,867,728 A | | 2/1975 | Stubstad et al. |
| 3,875,595 A | | 4/1975 | Froning |
| 4,309,777 A | | 1/1982 | Patil |
| 4,334,193 A | | 6/1982 | Gordy et al. |
| 4,349,921 A | | 9/1982 | Kuntz |
| 4,663,358 A | * | 5/1987 | Hyon et al. ............. 521/64 |
| 4,664,857 A | * | 5/1987 | Nambu ................. 264/28 |
| 4,714,469 A | | 12/1987 | Kenna |
| 4,734,097 A | * | 3/1988 | Tanabe et al. .......... 424/423 |
| 4,772,287 A | | 9/1988 | Ray et al. |
| 4,904,260 A | | 2/1990 | Ray et al. |
| 4,911,718 A | | 3/1990 | Lee et al. |
| 4,988,761 A | | 1/1991 | Ikada et al. |
| 5,007,934 A | | 4/1991 | Stone |
| 5,012,503 A | * | 4/1991 | Nambu et al. ............ 378/64 |
| 5,047,055 A | | 9/1991 | Bao et al. |
| 5,192,326 A | | 3/1993 | Bao et al. |
| 5,534,028 A | * | 7/1996 | Bao et al. ............. 623/17.16 |
| 5,705,780 A | | 1/1998 | Bao |
| 5,976,186 A | | 11/1999 | Bao et al. |
| 5,981,826 A | * | 11/1999 | Ku et al. ................ 623/23.72 |
| 6,060,534 A | * | 5/2000 | Ronan et al. .............. 523/113 |
| 6,187,048 B1 | | 2/2001 | Milner et al. |
| 6,264,695 B1 | | 7/2001 | Stoy |
| 6,268,405 B1 | * | 7/2001 | Yao et al. ................. 523/113 |
| 6,280,475 B1 | | 8/2001 | Bao et al. |
| 6,414,214 B1 | * | 7/2002 | Engelhardt et al. ......... 604/368 |
| 6,783,721 B2 | * | 8/2004 | Higham et al. .......... 264/328.1 |
| 7,098,463 B2 | * | 8/2006 | Adamovics ............. 250/474.1 |
| 2003/0080465 A1 | | 5/2003 | Higham et al. |

OTHER PUBLICATIONS

Yamaura K et al, Properties of Gels Obtained by Freezing/Thawing of Pol(vinyl Alcohol)/Water/Dimethyl Sulfoxide Solutions, 1989, J Appl Poly Sci, vol. 37, p. 2709-2718.*

Kobayashi M, A study of polyvinyl alcohol-hydrogel (PVA-H) artificial meniscus in vivo, 2004, BioMed Mater Eng, vol. 14, p. 505-515.*

Zheng-Qiu G et al, The development of artificial articular cartilage—PVA-hydrogel, 1998, BioMed Mater Eng, vol. 8, p. 75-81.*

Purss H K et al, Poly(vinyl alcohol) hydrogels: Their synthesis and steps towards control of electroendosmosis, 2003, Electrophoresis, vol. 24, p. 12-19.*

Structure and Properties of Poly (vinyl alcohol)-Iodine Complex Formed in the Crystal Phase of Poly (vinyl alcohol) Films, Y. Choi and K. Miyasaka, Journal of Applied Polymer Sciences, vol. 51, 613-618 (1994).

Hydrogels and Biodegradable Polymers for Bioapplications, Amercian Chemical Society, 1994.

Swelling Pressure of Poly (Glyceryl Methacrylate) Hydrogels, M. Refojo, pp. 697-704, 1972.

* cited by examiner

*Primary Examiner*—Christina Johnson
*Assistant Examiner*—Janis Sanders
(74) *Attorney, Agent, or Firm*—Lerner, David, Littenberg, Krumholz & Mentlik, LLP

(57) ABSTRACT

A wear resistant hydrogel for use as a prosthetic implant, such as for cartilage, is made by forming a solution of polyvinyl alcohol in a solvent of DMSO/water. The solution is placed in a mold and is gelated by cycling the mold in a freeze-thaw cycle at a temperature at or below 4° C. for a period of 2 to 24 hours. The hydrogel so formed is washed in a saline solution, including potassium carbonate. The hydrogel is then dehydrated to 20 to 70% water content and thereafter irradiated with Gamma radiation. The surface of the hydrogel is then cross-linked using a boric acid solution preferably between 2.5 and 5% for about 1 minute. The hydrogel is then rinsed and sterilized.

22 Claims, 4 Drawing Sheets

PVA HYDROGEL SAMPLE FABRICATED USING THE NOMINAL STEPS OUTLINED IN FIGURE 1 EXCEPT EXPOSED TO 25 kGy OF GAMMA IRRADIATION.
PORE SIZE IS 50-60 nm.

PVA HYDROGEL SAMPLE FABRICATED USING THE NOMINAL STEPS OUTLINED IN FIGURE 1 INCLUDING EXPOSURE TO 75 kGy OF GAMMA IRRADIATION.
PORE SIZE IS 30-50 nm.

AVERAGE CONSTANT VELOCITY FRICTION
FROM THE FIVE PATHWAYS
6 KM

AVERAGE CONSTANT VELOCITY FRICTION
FROM THE FIVE PATHWAYS
20 KM

WEAR RESISTANT HYDROGEL FOR BEARING APPLICATIONS

BACKGROUND OF THE INVENTION

This invention relates to surgical implants that are designed to replace meniscal tissue and cartilage in a mammalian joint, such as a knee joint, and methods to implant the same. While a knee is the primary joint of concern, the invention applies to other body joints such as the hip, shoulder, elbow, temporomandibular, sternoclavicular, zygapophyseal and wrist. More particularly, this invention relates to a wear resistant hydrogel for such applications.

Compared to the hip, the knee has a much greater dependence on passive soft tissues (menisci, ligaments and the joint capsule) for stability and function. Although the mechanics of the two joints are different, most known hip and knee implants are very similar in design, both consisting of a semi-rigid on rigid (polyethylene on cobalt chrome alloy) bearing surface. In many prosthetic knee implants, function and mobility are impaired because rigid structures are used to replace the natural soft tissues.

Normal anatomical knees joints have two pliable, mobile menisci that function to absorb shock, distribute stress, increase joint congruity, increase contact area, guide arthrokinematics, help lubrication by maintaining a fluid-film bearing surface, and provide proprioceptive input, i.e., nerve impulse via its attachment to the joint capsule. Even under physiologic loading a natural knee with natural menisci will primarily distribute stresses through a fluid film, only 10% of a load is transmitted via a solid on solid contact. Due to the fluid film bearing surface contact wear is greatly reduced. In simple terms the menisci function to reduce joint stresses, decrease wear, and help guide normal kinematics. Without menisci, peak contact stresses in the knee increase by 235% or more and degenerative changes start to progress rapidly. At 0°, 30° and 60° of flexion, natural knees with intact menisci have approximately 6 to 8 times the contact area of typical prosthetic knee implants many of which have a similar geometry to that of a natural knee without menisci.

Typical existing knee replacements lack the functional features normally provided by the menisci and the common polyethylene on metal such as cobalt chrome (CoCr) bearing interface lacks the wear-reducing fluid film bearing surface. By adding a well-designed meniscal substitute, many shortcomings of existing knee replacements can be addressed. In theory, prosthetic menisci could have the same impact on a prosthetic knee as natural menisci do for natural knees.

A prosthetic knee meniscus has at least one and preferably two compliant prosthetic menisci (medial and lateral in the knee) that are attached to the joint capsule and meniscal horns in a similar fashion to the way a natural meniscus is attached to a natural knee. Like a natural meniscus, the meniscal knee implant of the present invention will be able to pivot and glide on a prosthetic tibial plateau. Arthrokinematic constraint comes from the meniscal attachments and will gently guide movements, providing a highly mobile but stable joint. Also through its attachments, the anatomical meniscal-bearing knee will provide proprioceptive input, giving the central nervous system feedback for refined motor control.

In the past, effort mainly has been placed on the development of meniscal replacement. In the attempt to repair or replace torn menisci, allografts, xenografts and autografts have been implanted for over 20 years. Current focus has been on the development of collagen-matrix meniscal implants. However, these implants do not reproduce the mechanical properties of a normal meniscus.

As used herein, all references to "implants" or "implantation" (and all terms such as surgery, surgical, operation, etc.) refer to surgical or arthroscopic implantation of a reinforced or wear resistant hydrogel device, as disclosed herein, into a mammalian body or limb, such as in a human patient. Arthroscopic methods are regarded herein as a subset of surgical methods, and any reference to surgery, surgical, etc., includes arthroscopic methods and devices. The term "minimally invasive" is also used occasionally herein, even though it is imprecise, one should assume that any surgical operation will be done in a manner that is minimally invasive, in view of the needs of the patient and the goals of the surgeon.

Meniscal Tissues in Knees—Each knee joint of a human contains a "medial" meniscus and a "lateral" meniscus. The lateral meniscus is located on the outer side of the leg, directly above the location where the upper end of the fibula bone is coupled to the tibia ("shinbone"). The medial meniscus is located on the inner side of the leg.

Each meniscus (also referred to, especially in older texts, as a "semilunar fibrocartilage") has a wedged shape, somewhat comparable to a segment from an orange or other citric fruit, but with a substantially larger curvature and "arc." The thickest region is around the periphery (which can also be called the circumference, the rim, and similar terms). When implanted into a knee, this peripheral rim normally will be anchored to the surrounding wall of a fibrous "capsule" which encloses the knee joint and holds in the synovial fluid, which lubricates the cartilage surfaces in the knee. The two ends of each semi-circular wedge are coupled, via thickened collagen structures called horns to the "spine" protrusions in the center of the tibial plateau.

The inner edge of a meniscus is the thinnest portion of the wedge; this edge can also be called the apex, the margin, and similar terms. It is not anchored; instead, as the person walks or runs, each meniscus in a knee is somewhat free to move, as it is squeezed between the tibial plateau (beneath it) and a femoral runner or condyle (above it). The bottom surface of each meniscus is relatively flat, so it can ride in a relatively stable manner on top of the tibial plateau. The top surface is concave, so it can provide better, more closely conforming support to the rounded edge of the femoral runner. Because of its shape, location and ability to flex and move somewhat as it is pushed, each meniscus helps support and stabilize the outer edge of a femoral runner, as the femoral runner presses, slides and "articulates" against the portion of the tibial plateau beneath it.

However, because all four of the menisci inside a person's knees are in high-stress locations, and are subjected to frequently-repeated combinations of compression and tension (and sometimes abrasion as well, especially in people suffering from arthritis or other forms of cartilage damage), meniscal damage often occurs in the knees of humans, and occasionally other large animals.

It should also be noted that, in humans, meniscal-type tissues also exist in temporomandibular, sternoclavicular, zygapophyseal, and wrist joints.

Various efforts have been made, using prior technology, to repair or replace damaged meniscal tissue. However, because of the complex structures and anchoring involved, and because of the need to create and sustain extremely smooth and constantly wet surfaces on the inner portions of each meniscal wedge, prior methods of replacing or repairing damaged meniscal are not entirely adequate.

Many meniscal implants for the knee address the need for attachment to the surrounding soft tissue but they do not address the need to resurface the femoral and/or the tibial articulating surfaces. An example of this type of implant is described by Kenny U.S. Pat. No. 4,344,193 and Stone U.S. Pat. No. 5,007,934.

A free-floating cobalt chrome meniscal replacement has been designed to cover the tibial bearing surface. Because this implant is rigid and because it is disconnected from the soft tissues it lacks the ability to shock absorb and/or provide proprioceptive input. In fact, because it is approximately 10-20 times more rigid than bone it may actually cause concentrated loading, increased contact stresses, and therefore accelerate degenerative joint changes.

A hydrogel is a network of a hydrophilic polymer(s) in which a large amount of water is present. In general, the water content is at least 20% by weight. In order to keep the hydrogel from being dissolved by the water, the polymer network must be crosslinked either physically or chemically. The water content (and therefore physical size) of hydrogels with either or both types of crosslinks may be sensitive to a variety of environmental conditions depending on the polymer. These environmental conditions include pH, temperature, electric field, and ionic strength and type.

The flexible, pliable gel-like nature of a synthetic hydrogel (when saturated with water) arises mainly from crosslinking attachments between non-parallel fibers in the gel. Depending on the specific polymeric structure that has been chosen, these crosslinking attachments between the long "backbone" chains in a polymer can be formed by covalent bonding, by hydrogen bonding or similar ionic attraction, or by entangling chains that have relatively long and/or "grabby" side-chains.

Regardless of which type of bonding or entangling method is used to bind the backbone chains together to form a hydrogel, the "coupling" points between molecular chains can usually be flexed, rotated, and stretched.

In addition, it should be recognized that the back-bone chains in hydrogel polymers are not straight; instead, because of various aspects of interatomic bonds, they are somewhat kinked, and can be stretched, in an elastic and springy manner, without breaking the bonds.

In a typical hydrogel, the polymeric chains usually take up less than about 10% of the volume; indeed, many hydrogels contain less than 2% polymer volume, while interstitial spaces (i.e., the unoccupied spaces nestled among the three-dimensional network of fibers, which become filled with water when the gel is hydrated) usually make up at least 90 to 95% of the total volume. Accordingly, since the "coupling" point between any two polymeric backbone chains can be rotated and flexed, and since any polymeric backbone molecule can be stretched without breaking it, a supple and resilient gel-like mechanical structure results when a synthetic hydrogel polymer is hydrated.

Physically crosslinked hydrogels are semi-crystalline forms of the polymeric material. The crystalline domains are locations where the polymer chains are neatly packed. The crystalline domains are suspended in the amorphous (i.e., loosely packed, unordered) regions of the polymer, and in order for the crystalline domains to grow they must pull polymer chains from the amorphous regions. As the material becomes more crystalline the equilibrium water content is reduced. The material will continue to become more crystalline until the mobility of the polymer chains in the amorphous regions of the polymer is reduced to the point that they cannot be drawn into the crystalline structure. At this point the polymeric material has reached its equilibrium crystallinity. When using a hydrogel material in an implant, it can be advantageous to ensure that the polymeric material has reached its equilibrium crystallinity prior to being place in vivo so that the material properties and size are stable.

Certain types of ions can help to increase the rate at which polymer chains in the amorphous regions of the material are drawn into the crystalline regions and thus establishing equilibrium crystallinity. The ions that have the greatest effect will depend on the type of polymer. In addition, a greater concentration of ions may increase the rate of crystalline growth. In the case of polyvinyl alcohol hydrogel (PVA), potassium has a greater effect than sodium on the rate of crystallinity (as measured by mass change) when comparing cations. The carbonate ion has a greater effect than chloride when comparing anions. Therefore, potassium carbonate should have a greater effect than sodium chloride on the rate at which a PVA hydrogel will reach its equilibrium crystallinity.

Due to the high water content of hydrogels, there has been interest in using these materials in a variety of medical devices. These devices include those intended for both short (such as a cervical dilator) and long term (such as a non-throbogenic coating for vascular grafts) exposure to the body, and also both load bearing (such as an artificial articular cartilage) and non-load bearing devices (such as contact lenses).

Hydrogels have been used in biomedical applications, such as contact lenses and spinal implants. Among the advantages of hydrogels is that they are as biocompatible as hydrophobic elastomers and metals. This biocompatibility is largely due to the unique characteristics of hydrogels in that they are soft and contain water like the surrounding tissues and have relatively low frictional coefficients with respect to the surrounding tissues. The biocompatibility of hydrogels results in prosthetic nuclei which are more easily tolerated in the body. Furthermore, hydrophobic elastomeric and metallic gels will not permit diffusion of aqueous compositions, and their solutes, therethrough.

An additional advantage of some hydrogels is their good mechanical strength which permits them to withstand the load on the disc and restore the normal space between the vertebral bodies. The spinal nuclei of Bao et al. U.S. Pat. No. 5,047,055 have high mechanical strength and are able to withstand the body loads and assist in the healing of the defective annuli.

Other advantages of the hydrogels, used in the Bao et al. nuclei, are their excellent viscoeleastic properties and shape memory. Hydrogels contain a large amount of water which acts as a plasticizer. Part of the water is available as free water which has more freedom to leave the hydrogel when the hydrogel is partially dehydrated under mechanical pressure. This characteristic of the hydrogels enables them to creep, in the same way as the natural nucleus, under compression, and to withstand cyclic loading for long periods without any significant degradation or loss of their elasticity. This is because water in the hydrogel behaves like a cushion whereby the polymeric network of a hydrogel with a high EWC is less susceptible to damage under mechanical aid.

Another advantage of hydrogels is their permeability to water and water-soluble substances, such as nutrients, metabolites and the like. It is known that body fluid diffusion, under cyclic loading, is the major source of nutrients to the natural disc. If the route of this nutrient diffusion is blocked, e.g., by a water-impermeable nucleus, further deterioration of the disc will ensue.

In addition, the incision area on the annulus can be reduced, thereby helping heal the annulus and prevent the reherniation of the disc. Hydrogels are also useful for drug delivery into the disc due to their capability for controlled release of drugs. Various therapeutic agents, such as growth factors, long term analgesics, antibiotics and anti-inflammatory agents can attach to the prosthetic nucleus and be released in a controllable rate after implantation of the nucleus in the disc.

Furthermore, dimensional integrity can be maintained with hydrogels having a water content of up to about 90%. This dimensional integrity, if the nucleus is properly designed, will aid in distributing the vertebral load to a larger area on the annulus ring and prevent the prosthetic nucleus from bulging and herniating.

SUMMARY OF THE INVENTION

It is an object of this invention to provide a method for forming a highly wear resistant hydrogel implant.

It is another object of the invention to provide a wear resistant prosthetic meniscus.

These and other objects are achieved by a method for forming a high strength hydrogel medical implant which includes preparing a hydrogel solution, injecting the solution into a mold and causing the molded solution to gel. The preferred solution is a 15% polyvinyl alcohol solution in dimethyl sulfoxide (DMSO) and water. The preferred gelation method is a freeze-thaw cycle of cooling the solution in the mold to 4° C. or below for 2 to 24 hours (preferably −20° C.) and then thawing for 16 hours. This cycle is repeated up to five times preferably at least one time. The molded gel is then washed in a physiologic solution such as a saline solution for between two to twelve weeks. The saline solution may contain between 0.025 M and 0.25 M and preferably between 0.025 M and 0.05 M solution of potassium carbonate ($K_2CO_3$). Besides a solution containing potassium carbonate, any physiologic solution having an ionic charge could be used, for example, serum at a pH that would allow some or all proteins to be charged. During or after washing, the surface of the hydrogel may be chemically cross-linked using boric acid. After the hydrogel solution has been washed from between two to twelve weeks, it is dehydrated and packaged. By dehydration, it is meant that the water content of the hydrogel is reduced to about 55%. The saline solution used is preferably a 0.9% phosphate buffered sodium chloride solution to which the potassium carbonate is added at a concentration of between 0.025 M and 0.25 M.

The washing process may run from one day to twelve weeks and preferably from two to twelve weeks and most preferably for twelve weeks.

The saline solution is changed regularly, for example, two, three, five or more times a week during the washing process. In addition, the concentration of the potassium carbonate solution can be changed during the washing period with a more concentrated solution, 0.05 M solution being used during the first two to four weeks and then a lower concentration solution of about 0.025 M potassium carbonate being used for the last four to eight weeks of washing. Normally, the hydrogel is irradiated after washing in a hydrated state of about 75% water content.

It has been found that washing the hydrogel implants after gelation in a physiologic saline rather than water ensures that the swelling pressure characteristics of the material used in the artificial nucleus implant would remain stable after implantation. Results showing that washing the implants in saline creates a hydrogel material that does not undergo swelling pressure property changed in vivo. It has also been found that chemical crosslinking of the surface with boric acid or glutaraldehyde improves wear.

One of the most important properties of any load-bearing hydrogel implant is the swelling pressure characteristic (i.e. water content vs. externally applied pressure) of the material used in the implant. Early results from pre-clinical safety studies have shown that the swelling pressure characteristics of the water-washed PVA hydrogel was not constant during the first four weeks in vivo, with no further changes occurring at later time points. These changes indicate that the implant may have a lower in vivo equilibrium water content immediately after implantation than originally estimated, and would therefore have a smaller volume. This reduction in implant volume would have no bearing on the safety of the device, but could have an effect on the ability of the implant to maintain disc height. Maintenance of disc height is a parameter that may be assessed in a clinical study to evaluate efficacy of the implant.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

One of the most important properties of any load-bearing hydrogel implant is the swelling pressure characteristic of the material used in the implant. The swelling pressure characteristic of a hydrogel describes the relationship between applied load and equilibrium water content. In general, a larger load on the material will result in a reduced water content. This phenomenon has been well documented for the nucleus pulposus of the intervertebral disc, which is a hydrogel.

It is important for any load-bearing implant made from a hydrogel material to have a stable swelling pressure characteristic after implantation. If the swelling pressure characteristic of the implant changes over time it may be difficult to predict the equilibrium water content and size of the implant. Early results from a pre-clinical safety study evaluating an artificial nucleus pulposus implant made from a water-washed poly (vinyl alcohol) (PVA) hydrogel showed that the swelling pressure characteristic had changes compared to an unimplanted control after four week in vivo, with no further changes occurring at later time points.

Figure 1:
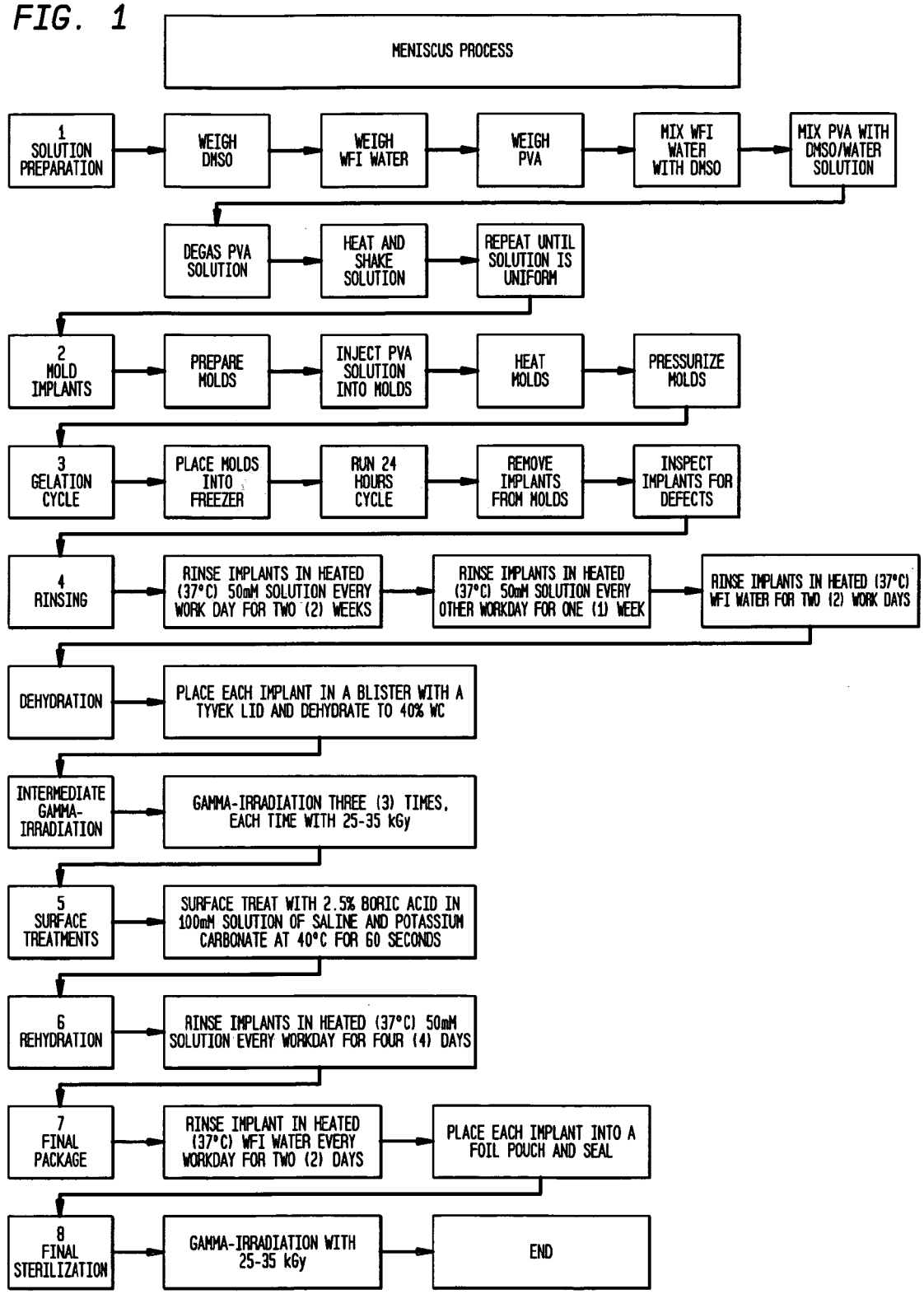
FIG. 1 is a material process flowchart depicting a preferred method of forming the hydrogel of the present invention.
Figure 2:
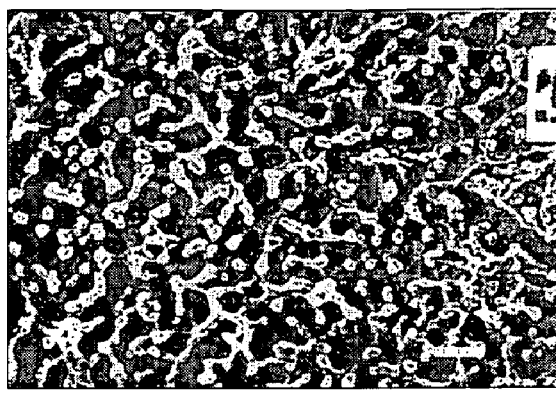
FIG. 2 shows a PVA hydrogel sample fabricated using the process of FIG. 1 irradiated at 25 kGy after dehydration with a pore size of 50 to 60 $N/mm^2$.

Washing the implants after gelation in a physiologic saline solution rather than water was adopted in order to ensure that the swelling pressure characteristics of the material used in the artificial nucleus implant would remain stable after implantation. This change to the method used to process the material was successful as shown in FIGS. 1 and 2. The results of washing the implants in saline on the swelling pressure characteristic can be seen at the one-month time point, and are merely confirmed by results from later time points.

It is preferred herein to use a hydrogel for replacing a wear surface such as a meniscus. An important property of such a hydrogel is the wear properties of the hydrogel surface. This can be enhanced by a two step crosslinking process.

EXAMPLE I

Formation of Bulk Hydrogel

The implants used in this study were fabricated in a class 1,000 clean room using the manufacturing flow chart of FIG. 1. The implants were molded from a solution in DMSO/water solvent, a 98.5% hydrolyzed (PVA-117, Kurray, Japan) poly (vinyl alcohol) (PVA) hydrogel that is physically crosslinked through the use of a freezing-thawing technique. This technique includes cooling the hydrogel in the mold to at or below 4° C. and holding at this temperature for 2 to 24 hours and then allowing the mold to warm to room temperature. Any water used in the fabrication of the device was USP Sterile Water-for-Injection (WFI) (Abbott Laboratories, North Chicago, Ill.).

The process for forming a more highly chemically crosslinked layer on the surface of a hydrogel was also used. This process provides for the formation of a transition zone between the more highly crosslinked surface and the less crosslinked bulk material. This transition zone makes it less likely that the surface will separate from the bulk material during repeated loading cycles.

A hydrogel with a more highly chemically crosslinked surface layer is for the purpose of imparting improved wear characteristics when articulating with tissue. Highly crosslinked materials are generally more brittle and have a relatively lower strain at material failure, properties which are often not desirable. Crosslinking only the surface of the hydrogel helps to preserve advantageous bulk properties of the hydrogel while making the material more resistant to wear.

The crosslinked surface layer is preferably formed by the diffusion of a crosslinking agent into the surface of the material. Preferably, the crosslinking agent is boric acid, however, glutaraldehyde could be used. The kinetics of the diffusion process results in a saturated surface layer (the highly crosslinked zone) and a gradient of crosslinking agent (boron) between the saturated surface layer and the bulk material not yet exposed to the agent (the transition zone).

The crosslinked surface layer is, in another embodiment, formed by e-beam irradiation sufficient to penetrate the surface but not pass through the bulk of the material. As the e-beam energy dissipates it will form a transition zone.

The highly crosslinked layer should be sufficiently thick for the application such that it will not be removed by any wear processes during the expected surface life, but not so thick that it significantly reduces the strain required to cause material failure.

EXAMPLE II

Step 1—Form A Bulk Hydrogel as in Example I by forming a solvent of approximately 75/25 wt/wt DMSO/water and placing a 15 wt % of PVA polymer was in the solvent.

The polymer/solvent solution was poured into a mold and the mold was placed in a freezer at below 0° C. preferably for about sixteen (16) hours and more preferably at 20° C. If desired, that freezing can take place for more than 16 hours.

The formed hydrogel was removed from the mold and placed in a saline solution preferably consisting of sodium chloride and potassium carbonate ions; and the hydrogel was washed in the saline solution preferably for about one week.

Step 2—Chemically Crosslink Surface Of Hydrogel of Step 1.

The hydrogel was dehydrated to approximately 40 wt % water saline solution.

The hydrogel was first irradiated with 10-40 kGy of gamma irradiation.

The hydrogel was then soaked in 1-5% boric acid in a saline solution for 30 seconds to 6 hours to form chemical crosslinks.

The surface cross-linked hydrogel was then soaked in a saline solution for about 4 days.

The hydrogel was then rinsed in water for about 2 days.

Step 3—Sterilize Hydrogel Part For Use In Medical Applications. A preferred sterilization process is shown in Example III.

EXAMPLE III

In the preferred method, a 15% solution of PVA was created in a solvent of 75/25 DMSO/water. A higher concentration of PVA will result in a material with a higher modulus of elasticity.

The preferred gelation cycle was one 16 hour soak at −20° C. However, up to 5 soak periods from 2 hours-24 hours each at any temperature at or below 4° C. can be used.

The hydrogel was then rinsed in 0.9% sodium chloride with phosphate buffer plus 50 mM potassium carbonate preferably for approximately 3 weeks. Other salts could also be used in the saline at higher or lower concentrations. Rinsing should proceed until the DMSO has been removed.

In the preferred embodiment, the hydrogel was then dehydrated to 40% water content and then irradiated with 75 kGy gamma irradiation. If the hydrogel is irradiated at a lower water content, a lower equilibrium water content and higher elastic modulus will result. However, as water content decreases, the effect becomes less pronounced. If less irradiation is used, a higher equilibrium water content and lower elastic modulus material will result. A water content range of 20%-70% and irradiation range of 5 kGy-100 kGy will produce an acceptable wear resistant hydrogel depending on the application. If a greater wear resistance is desired, one would make the surface more densely cross-linked and more deeply cross-linked by increasing the boric acid and time in the boric acid. However, this may make the material more brittle.

Surface crosslinking was then performed with the surface crosslinking preferably done at 40% water content with 2.5% boric acid solution for 60 seconds. If the crosslinking step is done at higher water content, a material with a higher equilibrium water content and lower elastic modulus will be created. A higher concentration of boric acid will create additional surface crosslinks. A longer soak time will result in a greater depth of penetration of the crosslinks. Water content ranges of 20%-70%, 0.1%-10% boric acid (or glutaraldehyde) concentrations (2.5-5% preferred) and 5 seconds-1 hour soak times (preferably 40-60 seconds), respectively produce an acceptable wear resistant hydrogel.

The hydrogel was then rehydrated in a 50 mM solution of $K_2CO_3$ at a temperature of about 37° C. for at least 3 days. After hydration the hydrogel is sterilized by, for example, gamma irradiation at 25-35 kGy for a total dose of 50-100 kGy. This can be performed after packaging.

Changing the parameters used in bulk material fabrication alters the microstructure density of the material. Wets thickness, pore size, pore volume. In general, a more dense microstructure will have a lower water content and higher elastic modulus. This is done by crosslinking at a lower water content. This ability to tailor the bulk material properties is independent of the ability to alter the amount and depth of penetration of surface crosslinks. FIG. 2 shows the polymeric microstructure (i.e. the water in the material has been removed) of two PVA hydrogels with different bulk microstructure. The images were obtained using the Quick Freeze/Deep Etch (QFDE) analysis technique.

Figure 4:
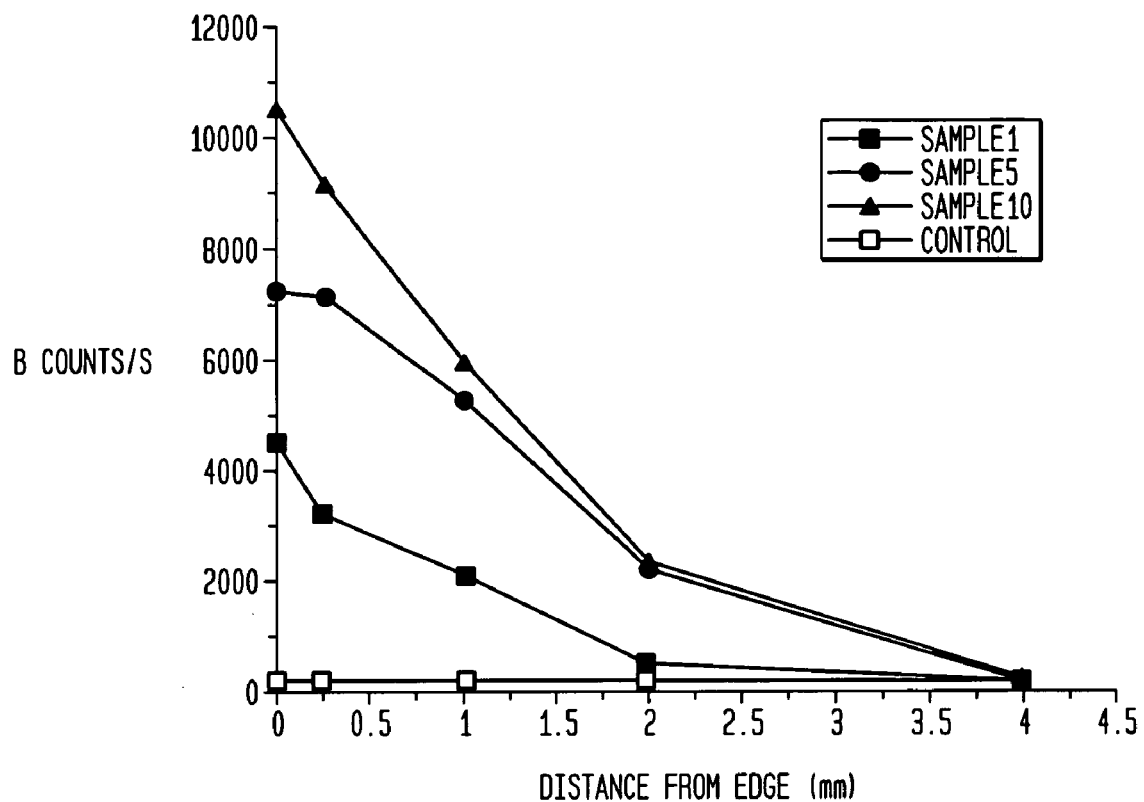
FIG. 4 shows a secondary ion mass spectroscopy analysis of three samples treated by the process of FIG. 1 and one control sample showing a gradient of boron from the surface to the inner bulk of a PVA hydrogel sample.

Testing was performed to show that the desired surface crosslinked material has been created and that it offers advantages with respect to friction against articular cartilage as compared to non-surface crosslinked material. Secondary ion mass spectroscopy (SIMS) was used to demonstrate that a gradient of boron existed in the material from the surface to the bulk. Additionally, longer soaking times lead to both greater depth of penetration and a higher concentration at the surface. FIG. 4 shows the SIMS results. A percentage of the boron incorporated in the material would be expected to exist within chemical crosslinks that would reinforce the material.

FIG. 4 shows a gradient of boron from the surface to the bulk in a PVA hydrogel sample produced by Example III. Data for soak time of 0 (control), 1, 5, and 10 minutes are shown.

Figure 3:
FIG. 3 shows a PVA hydrogel sample fabricated using the method of FIG. 1 with a 75 kGy radiation exposure after dehydration with a pore size of 30 to 50 $N/mm^2$.

The molding process produces a dense layer on the surface of the material. This dense layer works in conjunction with the surface crosslinking step to provide a tough outer "skin" that increases the suitability of this material for applications articulating against articular cartilage or other soft tissue. A QFDE image of the outer skin on the material in FIG. 3 exposed to a minimum of 75 kGy of gamma irradiation is shown in FIG. 5.

Figure 5:
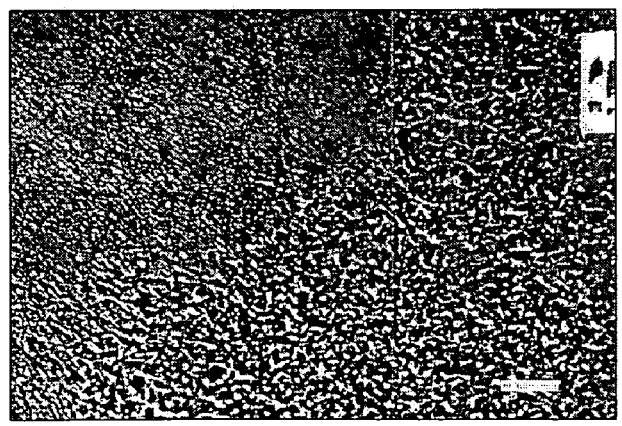
FIG. 5 shows a quick-freeze/deep etch (QFDE) analysis of a PVA hydrogel sample produced by the process of the present invention showing a dense outer "skin" with a scale bar of 200 $N/mm^2$.

FIG. 5 shows a QFDE image showing dense outer "skin" on the PVA hydrogel produced by Example III. The surface of the material is shown in the upper left quadrant, while the balance of the image shows an angled cut in to the subsurface. Scale bar is 200 nm.

Figure 6:
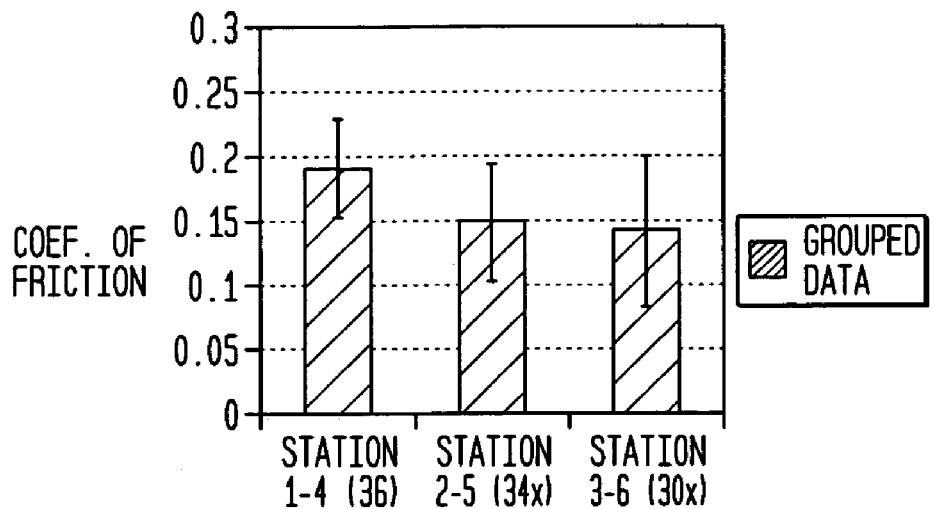
FIGS. 6 and 7 show hydrogel/cartilage friction data with FIG. 6 showing the friction immediately upon initiation of testing and FIG. 7 showing the friction data after 20 kilometers of sliding distance over the surface of the surface cross-linked hydrogel of the present invention. (Materials with an "X" designation have been surface cross-linked).
Figure 7:
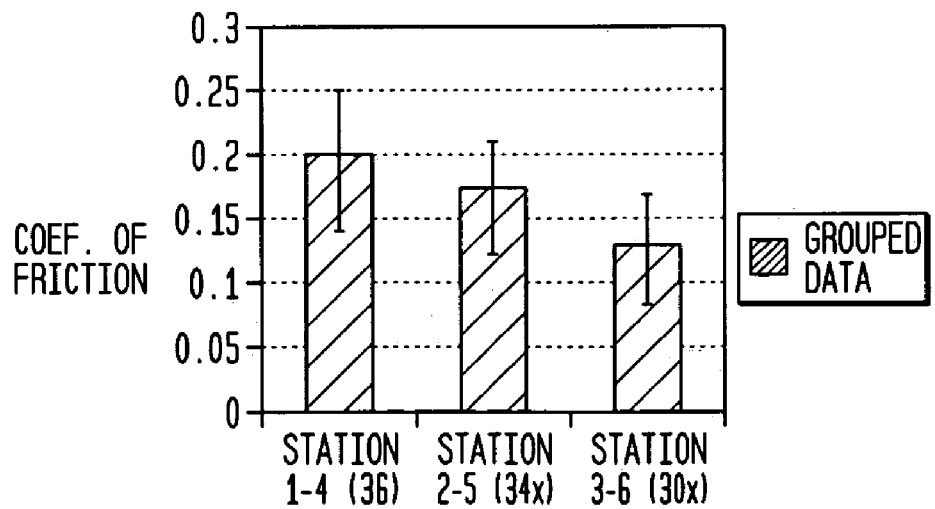

The surface crosslinking step has been shown to reduce the coefficient of friction of the material when articulating against rabbit femoral head cartilage. FIG. 6 shows the kinetic coefficient of friction of three PVA hydrogel materials against articular cartilage at both the start of the test and, in FIG. 2, after 20 km of sliding distance. A control hydrogel material (not surface crosslinked) was compared to two versions of the hydrogel that were surface crosslinked. The material designated "30X" was exposed to 25 kGy of gamma irradiation at approximately 70% water content, and "34X" was exposed to 75 kGy of gamma irradiation at 25% water content. As described above, 30X had a lower modulus of elasticity than 34X. FIGS. 6 and 7 indicate that both the surface crosslinking step and the bulk material processing steps may have an effect on the coefficient of friction under the test conditions. In addition, both surface crosslinked materials had a lower average coefficient of friction than the control material.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for making a wear resistant hydrogel comprising:
    forming a solution of poly (vinyl alcohol) polymer in a solvent made from water and an organic solvent;
    cooling the solution to below 0° C. to form the hydrogel;
    partially dehydrating the hydrogel;
    irradiating the partially dehydrated hydrogel in an oxygen reduced atmosphere;
    treating the surface of the partially dehydrated irradiated hydrogel with a solution containing a crosslinking agent selected from the group consisting of boric acid and glutaraldehyde in the presence of saline and carbonate ions; and
    thereafter rehydrating the hydrogel.

2. The method as set forth in claim 1, wherein the solvent for the poly (vinyl alcohol) is a mixture of water and DMSO.

3. The method as set forth in claim 2, wherein the solvent is about 25% water and about 75% DMSO.

4. The method as set forth in claim 1, wherein the solution is injected into a mold prior to cooling.

5. The method as set forth in claim 4, wherein the mold is frozen at about −20° C. for about 16 hours.

6. The method as set forth in claim 1, wherein the hydrogel is dehydrated to about 40% water content.

7. The method as set forth in claim 1, wherein said boric acid is a 2.5-5% acid solution.

8. The method as set forth in claim 1, wherein said hydrogel is soaked in said crosslinking solution for about 60 seconds at about 40° C.

9. The method as set forth in claim 1, wherein said irradiation is at a dose of about 25-35 kGy.

10. The method as set forth in claim 1, wherein said oxygen reduced atmosphere contains an inert atmosphere.

11. The method as set forth in claim 10, wherein the irradiation takes place in a nitrogen atmosphere.

12. The method as set forth in claim 1 further including soaking the hydrogel in a 50 mM$K_2CO_3$ solution prior to dehydrating.

13. The method as set forth in claim 12, wherein said soaked hydrogel is dehydrated to 40% water content prior to irradiating.

14. The method as set forth in claim 13 further including rehydrating the dehydrated hydrogel in a 0.9% phosphate buffered saline solution after soaking it in the boric acid solution.

15. The method as set forth in claim 14, wherein said washed hydrogel is dehydrated to about 40% water content.

16. The method as set forth in claim 1, wherein said hydrogel is irradiated at dose of about 25-35 kGy and thereafter soaked in the crosslinking solution at a sufficient concentration and for a sufficient time to induce chemical crosslinking of an outer surface of the hydrogel.

17. The method as set forth in claim 1, wherein rehydrating the hydrogel takes place by soaking the hydrogel for at least 3 days in a saline solution.

18. The method as set forth in claim 17 further including packaging and sterilizing after dehydration.

19. A method for making a prosthetic hydrogel implant for use in high wear applications comprising:
   forming a 5 to 20% solution of polyvinyl alcohol in a DMSO/water solvent;
   forming a hydrogel by gelating the solution in a mold by holding the solution for a period of 2 to 24 hours at a temperature at or below 4° C.;
   rinsing the hydrogel in a solution of sodium chloride, phosphate buffer and potassium carbonate;
   dehydrating the hydrogel to 20 to 70% water content;
   irradiating the dehydrated hydrogel in increments with a total dose of gamma irradiation of 50-100 kGy after dehydrating the hydrogel; and
   thereafter crosslinking the surface of the dehydrated hydrogel with a boric acid solution in the presence of carbonate ions and saline.

20. The method as set forth in claim 19 further including the step of heating and pressurizing the mold prior to gelating the solution.

21. The method as set forth in claim 19 wherein the dehydrated hydrogel is irradiated incrementally at between 25 kGy and 35 kGy to produce the total dose.

22. The method as set forth in claim 19 wherein the boric acid solution is a 2.5 to 5% solution and said surface is treated with said solution for about 40 to 60 seconds.

* * * * *